US00PP37830P2

(12) United States Plant Patent
Morgan

(10) Patent No.: US PP37,830 P2
(45) Date of Patent: Oct. 27, 2026

(54) ***LIMONIUM* PLANT NAMED '04LPS2007'**

(50) Latin Name: ***Limonium* hybrid**
Varietal Denomination: 04LPS2007

(71) Applicant: FlowerZone International Ltd, Auckland (NZ)

(72) Inventor: Edmund Morgan, Auckland (NZ)

(73) Assignee: FLOWERZONE INTERNATIONAL LTD, Auckland (NZ)

( * ) Notice: Subject to any disclaimer, the term of this patent is extended or adjusted under 35 U.S.C. 154(b) by 0 days.

(21) Appl. No.: 19/643,890

(22) Filed: Apr. 10, 2026

(51) Int. Cl.
*A01H 6/30* (2018.01)
*A01H 5/02* (2018.01)

(52) U.S. Cl.
USPC ..... Plt./358

(58) Field of Classification Search
USPC ..... Plt./263.1, 358
See application file for complete search history.

(56) References Cited

U.S. PATENT DOCUMENTS

PP33,240 P2 * 7/2021 van Steijn ..... Plt./339

* cited by examiner

*Primary Examiner* — Karen M Redden
(74) *Attorney, Agent, or Firm* — Penny J. Aguirre

(57) ABSTRACT

A new cultivar of *Limonium* plant named '04LPS2007' that is characterized by its reliable perennial habit in New Zealand, its flowers with sepals that are pastel blue lavender in color, its consistent repeated flower stem production throughout the summer and autumn seasons, its flowering stems that are 65 to 75 cm in length, and its tolerance to powdery mildew.

3 Drawing Sheets

Botanical classification: *Limonium* hybrid.
Cultivar designation: '04LPS2007'.

CROSS-REFERENCE TO RELATED APPLICATIONS

This application is co-pending with U.S. Plant Patent Applications filed for plants derived from the same breeding program that are entitled *Limonium* Plant Named '08LPS8' (U.S. Plant patent application Ser. No. 19/643,893), *Limonium* Plant Named '08LPS9' (U.S. Plant patent application Ser. No. 19/643,908), and *Limonium* Plant Named '08LPS14' (U.S. Plant Pat. Ser. No. 19/643,921).

BACKGROUND OF THE INVENTION

The present invention relates to a new and distinct cultivar of *Limonium*, botanically of hybrid origin and known as *Limonium* '04LPS2007' and hereinafter referred to by its cultivar name '04LPS2007'. '04LPS2007' is a new cultivar of statice, a perennial grown for use in containers and cut flower production.

The new cultivar arose from an ongoing breeding program by the Inventor in Palmerston North, New Zealand with the goal of using embryo rescue techniques to create new and unique cultivars of interspecific *Limonium*. The new cultivar resulted from embryo rescue of seeds of an unpatented proprietary *Limonium* plant of hybrid origin as the female parent, designated breeder code PsPs1, in Palmerston North, New Zealand in spring of 2004. The female parent had been hand pollinated from various unpatented proprietary plants of *Limonium sinuatum* from the Inventor's breeding program in spring of 2004. The seeds had been pooled from the crosses and therefore the male parent of '04LPS2007' is unknown. '04LPS2007' was selected as a single unique plant from the crosses in spring of 2005.

Asexual propagation of the new cultivar was first accomplished under the direction of the Inventor by tissue culture initiated from meristem tissue in summer of 2010 in Palmerston North, New Zealand. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '04LPS2007' as a new and unique cultivar of *Limonium*.

1. '04LPS2007' exhibits a reliable perennial habit in New Zealand.
2. '04LPS2007' exhibits flowers with sepals that are pastel blue lavender in color.
3. '04LPS2007' exhibits consistent repeated flower stem production throughout the summer and autumn seasons.
4. '04LPS2007' exhibits flowering stems that are 65 to 75 cm in length.
5. '04LPS2007' exhibits a tolerance to powdery mildew.

The female parent of '04LPS2007' differs from '04LPS2007' in having blooms with a different color, shorter flowering stems, and a different branching pattern. '04LPS2007' can be most closely compared to *Limonium perezii* 'Purple Parachute' (not patented) and *Limonium latifolium* 'Misty Blue' (not patented). 'Purple Parachute' differs from '04LPS2007' in having shorter flowering stems, flowers with purple sepals, and leaves that are wider and shorter. 'Misty Blue' differs from '04LPS2007' in having much smaller flowers that lack a pleasant fragrance and stems that are more branched with an airy habit.

'04LPS2007' can also be compared to the co-pending cultivars of *Limonium* '08LPS8', '08LPS9', and '08LPS14'. '08LPS8' differs from '04LPS2007' in having flowers with sepals that are medium to dark blue in color. '08LPS9' differs from '04LPS2007' in having flowers with sepals that are light grey to light pink in color with bases that turn dark pink in cooler months. '08LPS14' differs from '04LPS2007' in having flowers with sepals that are dark lavender in color.

BRIEF DESCRIPTION OF THE DRAWINGS

The accompanying color photographs illustrate the overall appearance and distinct characteristics of the new *Limonium*. The photograph was taken of a plant 4 months in age as grown outdoors in a 19-cm container in Heerhugowaard, The Netherlands.

The photograph in FIG. 1 provides a side view of the plant of '04LPS2007' in bloom.

Figure 1:
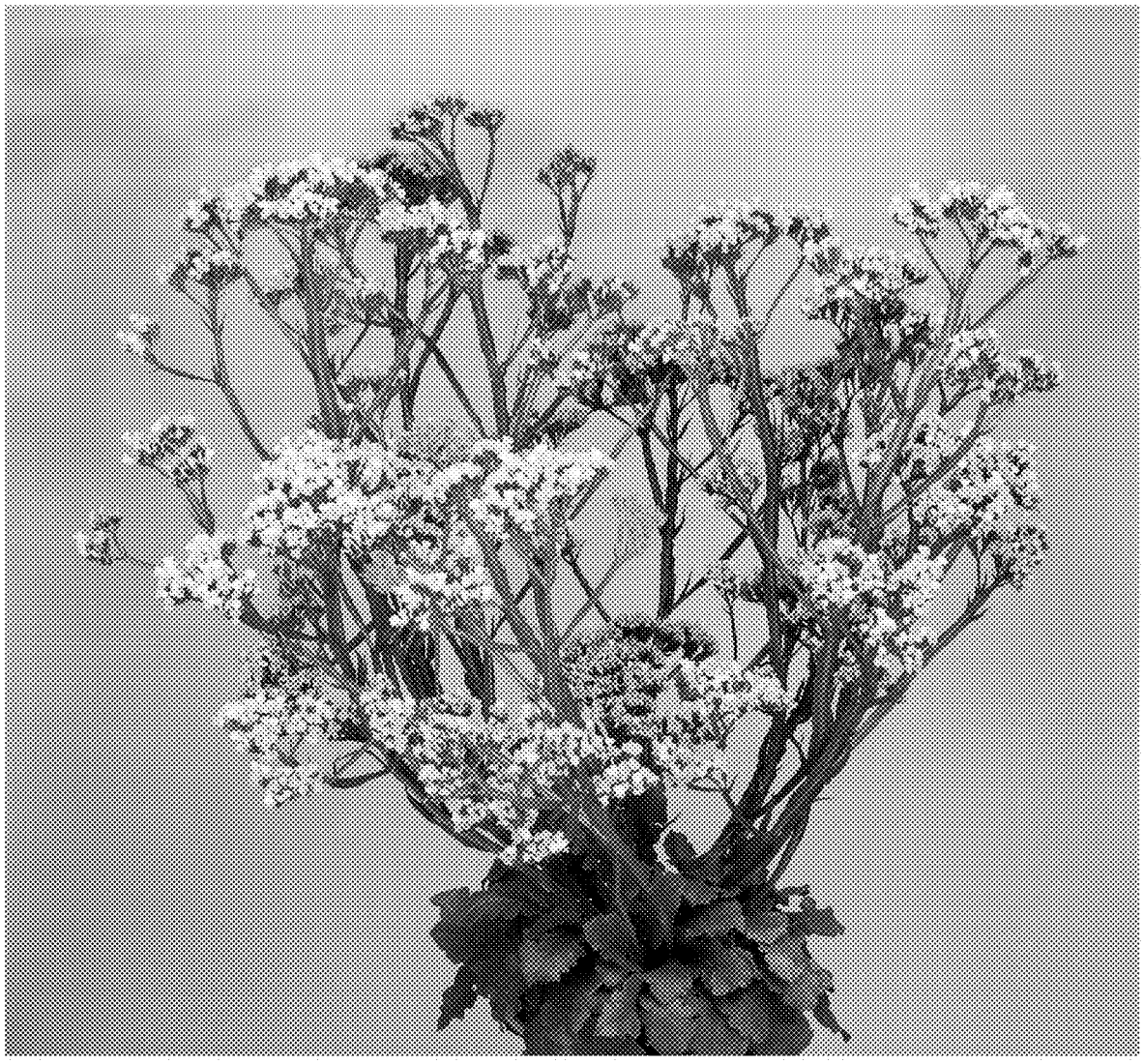
Figure 2:
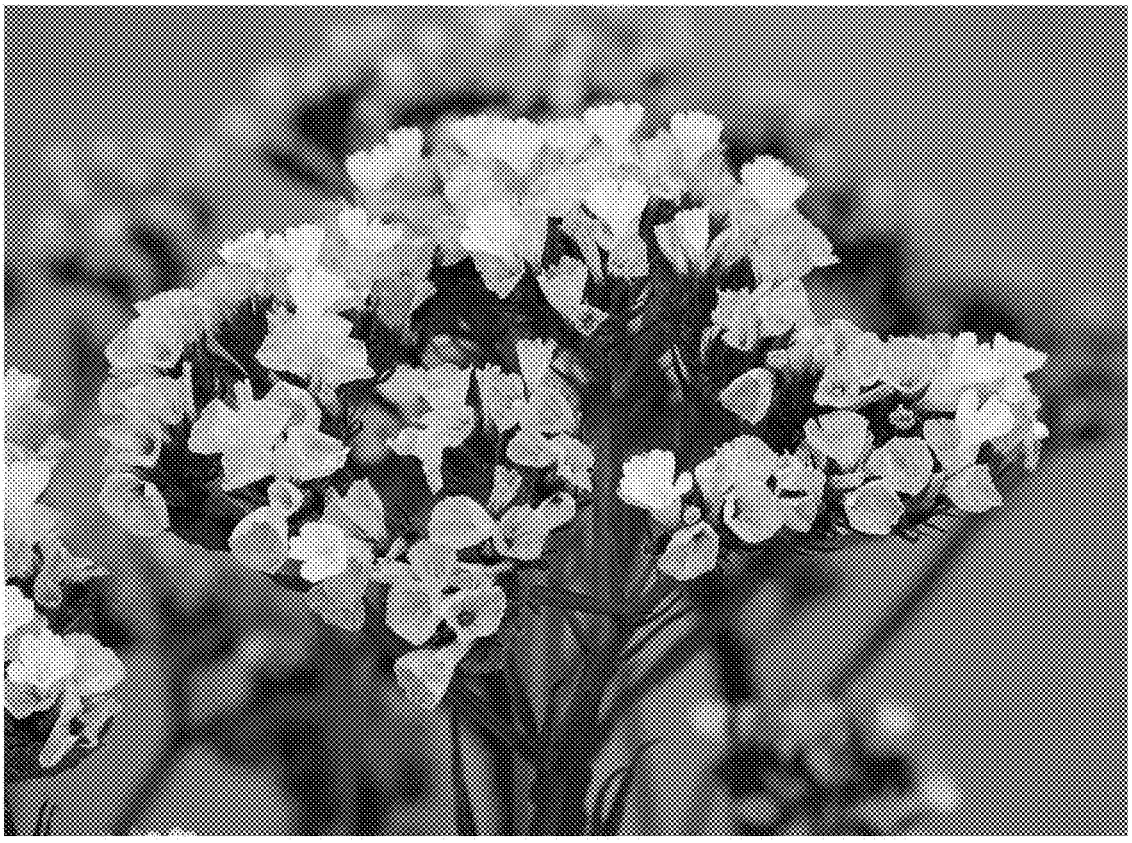

The photograph in FIG. 2 provides a close up of an inflorescences of '04LPS2007'.

Figure 3:
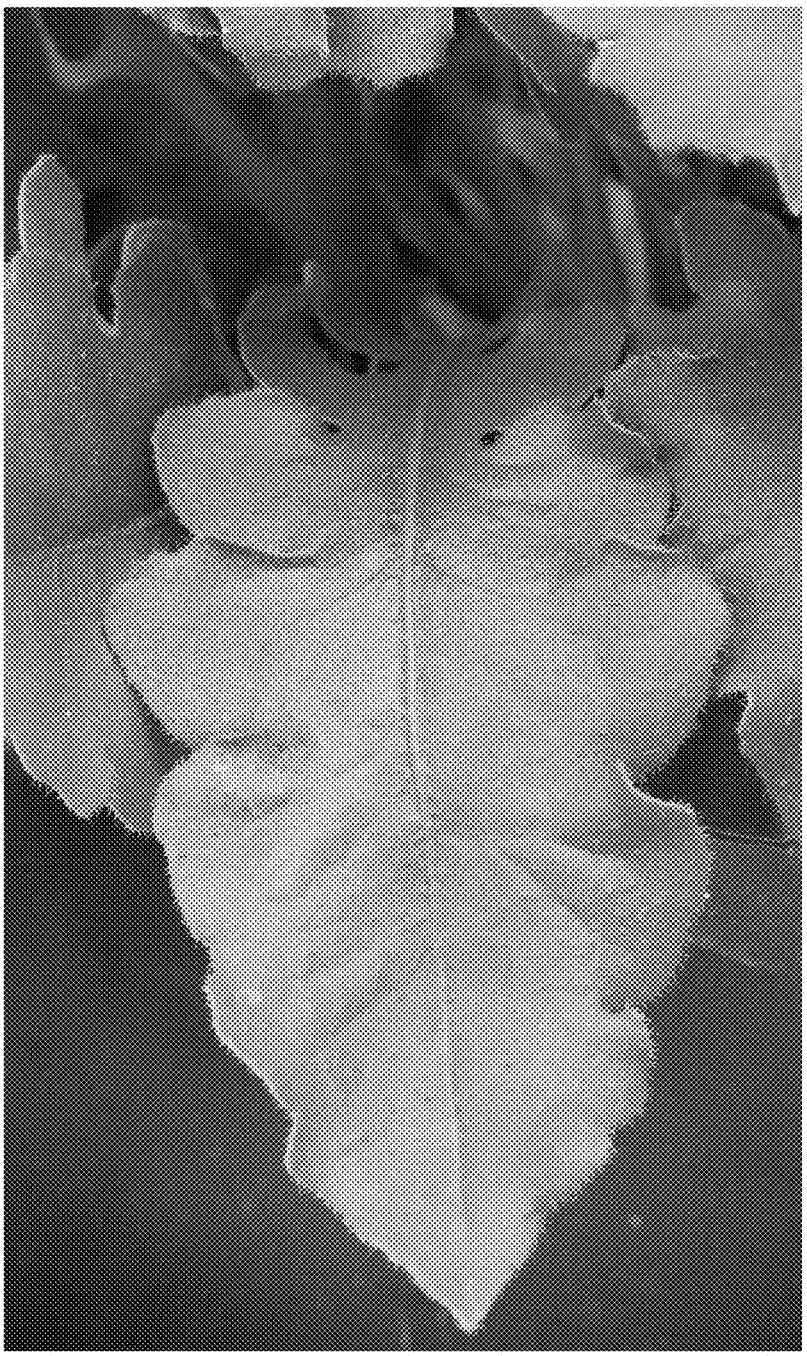

The photograph in FIG. 3 provides a close up of the foliage of '04LPS2007'.

The colors in the photograph are as close as possible with the digital photography techniques available, the color values cited in the detailed botanical description accurately describe the colors of the new *Limonium*.

DETAILED BOTANICAL DESCRIPTION OF THE PLANT

The following is a detailed description of 4-month-old plants of the new cultivar as grown outdoors in 19-cm containers in Heerhugowaard, The Netherlands. The phenotype of the new cultivar may vary with variations in environmental, climatic, and cultural conditions, as it has not been tested under all possible environmental conditions. The color determination is in accordance with the 2019 (reprint of 2025 6th edition) of The Colour Chart of The Royal Horticultural Society, London, England, except where general color terms of ordinary dictionary significance are used.

General description:

*Blooming period*.—Flowering commences in 6 to 8 weeks from a planted plug, flowering continues into autumn on new flowering stems, flowering can be extended if greenhouse grown.

*Plant type*.—Herbaceous perennial.

*Plant habit*.—Upright and broadly spreading.

*Height and spread*.—An average of 22.5 cm in height (soil level to top of foliar plane), an average of 62.5 cm in height (soil level to top of floral plane), and 72.4 cm in spread as grown in a 19-cm container, stems typically reach 65 to 75 cm in length in cut flower production fields.

*Hardiness*.—At least in U.S.D.A. Zones 8 to 11.

*Diseases and pests*.—Tolerance to powdery mildew caused by *Erysiphe polygoni* has been observed, no susceptibility or resistance to pests has been observed.

*Environmental stresses*.—Drought resistant.

*Root description*.—Fibrous roots on woody rootstalks.

*Propagation*.—Tissue culture.

*Root development*.—Plugs establish in 4 weeks from stage 3 tissue culture plantlets.

*Growth rate*.—Moderate to high.

Branch description (peduncle, flowering stem):

*Branch shape*.—Flattened with wings; 2 or 3, 2 mm in width, entire margins, NN137C in color.

*Branch color*.—137C to 137D.

*Branch size*.—56.2 cm in length and 5.5 mm in diameter as a 4-month-old plant in a container.

*Branch strength*.—Sturdy.

*Branch angle* (*to soil level*).—Main; 65° (varying between 40° and 90°), secondary; 35° (varying between 30° and 50°).

*Branch surface*.—Slightly glossy, smooth, glabrous.

*Branch number*.—Average of 13.

*Branching habit*.—Flowering stems emerge from basal rosettes.

Foliage description:

*Leaf shape*.—Obovate.

*Leaf division*.—Simple.

*Leaf base*.—Sheathing.

*Leaf apex*.—Short apiculate to abruptly acute with mucronate tip.

*Leaf venation*.—Pinnate, upper surface 146C and 146D, lower surface 146D.

*Leaf margins*.—Irregular angulate, moderately covered in very short hairs; average of 0.8 mm in length, color is not measurable.

*Leaf attachment*.—Sessile.

*Leaf arrangement*.—Alternate in basal rosettes.

*Leaf surface*.—Both surfaces smooth and glabrous, covered with a thin waxy layer 190A in color, veins sparsely pubescent; 0.8 mm in length, color is not measurable.

*Leaf color*.—Young upper surface; 144A, main vein 147D, mucronate tip 179A, young lower surface; 143C, main vein 145C, mucronate tip 179A, mature upper surface; a blend of NN137B and NN137C, mucronate tip 187C, mature lower surface; NN137C, mucronate tip 187C.

*Leaf size*.—An average of 16 cm in length and 8.4 cm in width.

*Leaf aspect*.—Flat to slightly curved downward.

*Leaf quantity*.—30 per basal rosette.

*Petioles*.—None.

*Stipules*.—None.

Flower description:

*Inflorescence type*.—Numerous small bell-shaped flowers arranged on compound corymbs on peduncles emerging from a basal rosette.

*Cut flowers*.—Suitable as cut flowers, average of 13 stems harvested per year.

*Inflorescence size*.—An average of 39.8 cm in height and 31.1 cm in diameter.

*Inflorescence number*.—An average of 7 per stem.

*Flower fragrance*.—Faint, sweet and pleasant.

*Flower quantity*.—Average of 1,900 flowers per inflorescence, 10,000 per plant.

*Flower lastingness*.—Average of four weeks, persistent.

*Flower buds*.—Lanceolate in shape, 9 mm in length, 2 mm in diameter, color; 90C, base 146D with bracts 63B, surface smooth, glabrous and very slightly glossy.

*Flower type*.—Rotate, single, consisting of one whorl of petals and one whorl of sepals.

*Flower aspect*.—Upright to very slightly outward.

*Flower size*.—Average of 4 mm in height and diameter, 1.5 cm in depth.

*Calyx*.—1.3 cm in length and 0.65 cm in width.

*Sepals*.—Average of 5, average of 1 cm in length, broadly obtuse apex, 100% fused into campanulate shape with tubular base, both surfaces smooth, glabrous, slightly glossy and slightly papery, color: upper and lower surface when opening and fully open; (campanulate part) N88D (slightly veined N88C on upper surface), tinged at base 51C, (tubular part) 145C.

*Petals*.—5, rotate in arrangement, 1 whorl, 1.3 cm in length, 2 mm in width, narrowly spathulate in shape, narrowly cuneate base, entire margins, both surfaces smooth, glabrous and slightly glossy, color; when opening and fully open upper and lower surface; a blend of 4D and 155A, lower 75% (narrow part of petal) NN155D.

*Floral bracts*.—At the base of each calyx a single bract is placed, oblong in shape, apex acute, base cuneate, 6 mm in length, 2 mm in width, surfaces are smooth and glabrous and slightly glossy, entire margins, color; both surfaces 144B and 144C, apex 63A.

*Pedicels*.—None, flowers are sessile to secondary peduncles.

Reproductive organs:

*Gynoecium*.—Pistils; 5, 9 mm in length, stigma; pointed in shape, NN155D in color, style; an average of 8.7 mm in length and NN155D in color, ovary; 153D in color.

*Androecium*.—Stamens; 5, anthers; dorsifixed, oblong in shape, 1 mm in length, 0.4 mm in width, color; 1C, filament; 9 mm in length and NN155D in color, pollen; low in quantity and 1D in color.

*Fruit and seed*.—No fruit or seeds have been observed to date.

It is claimed:

1. A new and distinct cultivar of *Limonium* plant named '04LPS2007' as herein illustrated and described.

* * * * *